US009730964B2

(12) United States Patent
Vesey et al.

(10) Patent No.: US 9,730,964 B2
(45) Date of Patent: Aug. 15, 2017

(54) PHARMACEUTICAL COMPOSITIONS AND TOPICAL USE THEREOF

(75) Inventors: Graham Vesey, Hornsby (AU); Rebecca Anne Webster, Avalon (AU)

(73) Assignee: Cell Ideas Pty Ltd., Gordon (AU)

( * ) Notice: Subject to any disclaimer, the term of this patent is extended or adjusted under 35 U.S.C. 154(b) by 0 days.

(21) Appl. No.: 14/005,269

(22) PCT Filed: Mar. 15, 2012

(86) PCT No.: PCT/AU2012/000274
§ 371 (c)(1),
(2), (4) Date: Nov. 21, 2013

(87) PCT Pub. No.: WO2012/122604
PCT Pub. Date: Sep. 20, 2012

(65) Prior Publication Data
US 2014/0087001 A1 Mar. 27, 2014

(30) Foreign Application Priority Data

Mar. 15, 2011 (AU) .............................. 2011900932
Jan. 13, 2012 (AU) .............................. 2012900140

(51) Int. Cl.
*A61K 35/32* (2015.01)
*A61K 35/36* (2015.01)
*A61K 35/35* (2015.01)
*A61K 35/28* (2015.01)

(52) U.S. Cl.
CPC .............. *A61K 35/35* (2013.01); *A61K 35/28* (2013.01)

(58) Field of Classification Search
CPC .................................................. A61K 35/35
See application file for complete search history.

(56) References Cited

U.S. PATENT DOCUMENTS

| 4,296,099 | A  | 10/1981 | Berrebi et al. |
| 2003/0147831 | A1 | 8/2003 | Marko |
| 2012/0207790 | A1 | 8/2012 | Maruyama et al. |

FOREIGN PATENT DOCUMENTS

| AU | 2009201915 | 9/2009 |
| AU | 2009251017 | 7/2011 |
| EP | 2 280 064 | 2/2011 |
| JP | 2005-519591 | 7/2005 |
| JP | 2007-512226 | 5/2007 |
| KR | 100995133 | 11/2010 |
| WO | 2005013885 A2 | 2/2005 |
| WO | WO 2005013885 A2 * | 2/2005 |
| WO | WO 2005/035742 | 4/2005 |
| WO | 2007026356 A2 | 3/2007 |
| WO | WO 2007026356 A2 * | 3/2007 |
| WO | 2008060374 A2 | 5/2008 |
| WO | WO 2008060374 A2 * | 5/2008 |
| WO | WO 2009/135907 | 11/2009 |
| WO | 2010020005 A1 | 2/2010 |
| WO | WO 2010020005 A1 * | 2/2010 |
| WO | WO 2011/043136 | 4/2011 |
| WO | WO 2011/136433 | 11/2011 |
| WO | WO 2012/047733 | 4/2012 |

OTHER PUBLICATIONS

Fu et al. (2007) Wound Repair and Regeneration, vol. 15: 540-548.*
Desmond et al. (2005) J. Investig. Dermatol Symp. Proc. 10: 184-189.*
Rhodes et al. (1998) Dermatol. Surg. 24(12): 1330-1332.*
Yamane et al. (2011) Biochem. Biophys. Res. Comm. 415: 235-238.*
Raskin et al. (2004) Current Pharmaceutical Design, 10, 3419-3429.*
Revilla et al. (1998) J. Agric. Food Chem. 46, 4592-4597.*
Fu, et al., "Adipose tissue extract enhances skin wound healing", 2007, Wound Repair and Regeneration, 15:540-548.
Kim et al., "Protective role of adipose-derived stem cells and their soluble factors in photoaging", Archives of Dermatological Research, 301(5):329-336. (Jun. 2009; Epub Apr. 2009).
Park et al., "Adipose-Derived Stem Cells and Their Secretory Factors as a Promising Therapy for Skin Aging", Dermatologic Surgery, 34(10):1323-1326. (Oct. 2008; Epub Jun. 2008).
Shamban, "Current and New Treatments of Photodamaged Skin", Facial Plastic Surgery, 25(5):337-349. (Dec. 2009).
Su Liqing, "Research progress on secretory functional characterization of adipose tissues", Foreign Medical Sciences Geriatrics) 28(5):228-31 (Sep. 2005). Chinese language document. English translation of Abstract provided.
Sun et al., "The pathogenesy and therapy medicine of acne", Chinese Pharmaceutical Association 2008 Annual conference Proceedings, pp. 573-577 (Dec. 2008). Chinese language document. English translation of Abstract provided.
Yang et al."Potential application of adipose-derived stem cells and their secretory factors to skin: Discussion from both clnical and industrial viewpoints", Expert Opinion on Biological Therapy, 10(4):495-503. (Apr. 2010).
Saito, "Acne and Skin Care" Pediatrics of Japan, 45(5):1007-1011 (2004). English translation of Abstract provided.
Toda, "Common Skin Diseases—First Choice Treatment for Physicians—Acne", Medicina, 37(4):604-607 (2000). English translation of Abstract provided.

* cited by examiner

*Primary Examiner* — Chris R Tate
*Assistant Examiner* — Russell Fiebig
(74) *Attorney, Agent, or Firm* — McDonnell Boehnen Hulbert & Berghoff LLP

(57) ABSTRACT

The present invention relates to methods for the preparation of compositions comprising adipose tissue-derived secretions, for example those derived from bovine adipose tissue, and the use of such compositions in the preparation of a pharmaceutical composition for topical use. The invention also relates to the use of adipose tissue-derived secretions and pharmaceutical compositions thereof for the topical treatment of a non-inflammatory condition, for example the treatment of a skin condition, and for the stimulation of hair growth in a subject by topical application. The invention also relates to the use of adipose tissue-derived secretions and pharmaceutical compositions thereof for the topical treatment of acne.

7 Claims, 2 Drawing Sheets

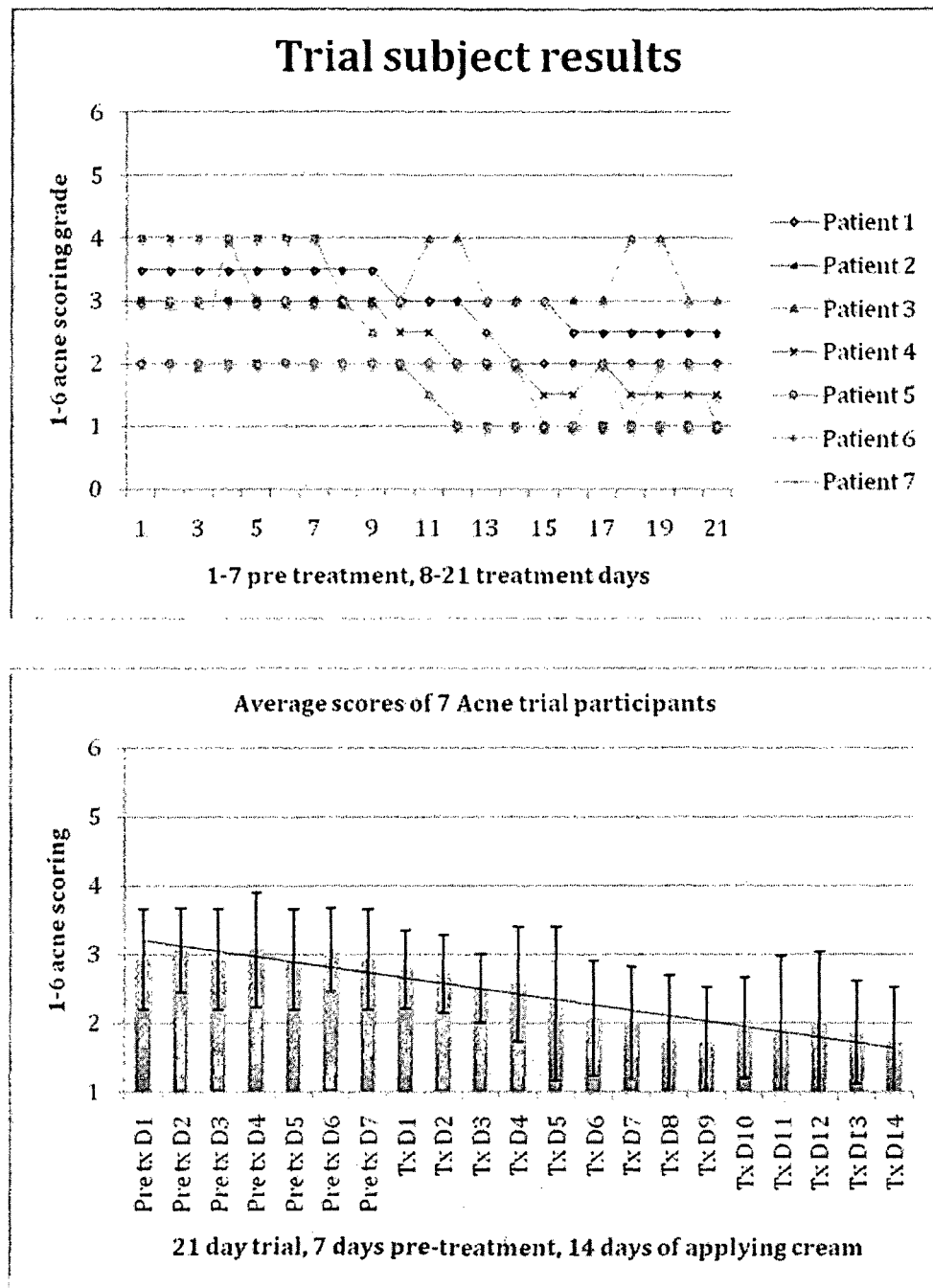
Figure 2 (A and B)

PHARMACEUTICAL COMPOSITIONS AND TOPICAL USE THEREOF

INCORPORATION BY CROSS-REFERENCE

This application claims priority from Australian provisional patent application number 2011900932 (AU 2011900932) filed on 15 Mar. 2011 and Australian provisional patent application number 2012900140 (AU 2012900140) filed on 13 Jan. 2012. The entire contents of AU 2011900932 and AU 2012900140 are incorporated by cross-reference.

TECHNICAL FIELD

The present invention relates to methods for the preparation of compositions comprising adipose tissue-derived secretions, for example those derived from bovine adipose tissue, and the use of such compositions in the preparation of a pharmaceutical composition for topical use. The invention also relates to the use of adipose tissue-derived secretions and pharmaceutical compositions thereof for the topical treatment of a non-inflammatory condition, for example the treatment of a skin condition, and for the stimulation of hair growth in a subject by topical application. The invention also relates to the use of adipose tissue-derived secretions and pharmaceutical compositions thereof for the topical treatment of acne.

BACKGROUND OF THE INVENTION

Adipose tissue contains a cell population of large, lipid-filled adipocytes and a population of non-adipocyte cells, which comprises cells associated with various connective fibres and cells associated with capillaries and larger blood vessels. The non-adipocyte cell population also comprises a variety of infiltrating immune cells and cells and cell processes associated with the nervous system. The non-adipocyte cell population is also thought to comprise a population of adipose-derived adult stem cells and consequently there has been interest in using adipose tissue as a source of isolated adult stem cells for various therapeutic applications.

In general, methods for obtaining adipose tissue-derived presumptive adult stem cells involves depleting adipocytes from adipose-derived non-adipocyte cells, which requires digesting adipose tissue with enzymes such as collagenase, and then separating the liberated cells by centrifuging the digested sample. During centrifugation, the adipose-derived non-adipocyte cells separate from the adipocytes to form a pellet, whereas the lipid containing adipocytes float. The fraction containing the non-adipocyte cells is then used as a source of tissue stem cells.

The present inventors have earlier described the use of an adipose tissue-derived cell suspension which comprises adipocytes for the preparation of a pharmaceutical composition for use in the treatment of an inflammatory disorder or the alleviation of pain associated with an inflammatory disorder in a subject, and for the treatment and alleviation of pain of conditions such as a cartilage or bone disorders. This is described in Australian Patent Application No. 2009201915 and in International Publication No. WO2010/020005, the contents of which are incorporated herein by cross-reference. There remains a need for improved methods for the treatment of non-inflammatory conditions and compositions for use therein.

Acne, including acne vulgaris and cystic acne, is a common skin disease. The areas of the skin commonly affected by acne include the face, the upper part of the chest, and the back. Acne most commonly occurs during adolescence, often continuing into adulthood. Various treatments are available for acne but, given the potential for acne scarring and for psychological effects on sufferers, who are often adolescents, alternative or improved treatments are desirable.

SUMMARY OF THE INVENTION

The inventor has surprisingly identified that secretions from adipose tissue-derived cells, including from adipocytes, are effective for improving various non-inflammatory conditions, for stimulating the growth of hair, wool and fur, and for the treatment or prevention of acne. The adipose tissue-derived cells from which the secretions are prepared may or may not comprise adipocytes.

In a first aspect of the invention there is provided use of a composition comprising adipose tissue-derived secretions in the manufacture of a medicament for the topical treatment of a non-inflammatory disorder in a subject.

In a second aspect there is provided a method of treating a non-inflammatory disorder in a subject, the method comprising topically administering to the subject a pharmaceutical composition comprising adipose tissue-derived secretions together with a pharmaceutically-acceptable carrier or diluent.

In an embodiment the non-inflammatory disorder is associated with one or more of the following conditions in said subject (i) dry skin, (ii) itchy skin, (iii) insect bite, (iv) sun burn, (v) wrinkling of the skin, (vi) thin skin, (vii) cracking of the skin, (viii) insect sting (ix) scarring, (x) stretch marks, (xi) sun spots, (xii) age spots, (xiii) liver spots, (xiv) puffiness and or dark circles around the eyes, (xv) athlete's foot, (xvi) warts, and said treatment alleviates one or more of said conditions.

In a third aspect there is provided use of adipose tissue-derived secretions in the manufacture of a medicament for topical use in stimulating hair, fur or wool growth in a subject.

In a fourth aspect there is provided a method of stimulating hair, wool or fur growth in a subject, the method comprising topically administering to the subject a pharmaceutical composition comprising adipose tissue-derived secretions, together with a pharmaceutically-acceptable carrier or diluent.

In an embodiment the subject has one or more of (i) surgery-related hair loss, (ii) chemotherapy-related hair loss, (iii) radiation exposure-related hair loss, (iv) alopecia, (v) male pattern baldness, (vi) female pattern baldness.

In a fifth aspect there is provided use of a composition comprising adipose tissue-derived secretions in the manufacture of a medicament for the topical treatment or prevention of acne in a subject. In an embodiment the medicament is for the treatment or prevention of acne in an adolescent.

In sixth aspect there is provided a method of treating or preventing acne in a subject, the method comprising topically administering to the subject a pharmaceutical composition comprising adipose tissue-derived secretions, together with a pharmaceutically-acceptable carrier or diluent.

In an embodiment the subject is an adolescent. In an embodiment the subject has clinically relevant acne. In an embodiment the acne is cystic acne. In an embodiment the subject has severe acne. In an embodiment the subject is an adolescent with clinically relevant acne.

The embodiments of the invention described herein apply to all aspects of the invention, as relevant.

In an embodiment the medicament or pharmaceutical composition for topical administration is a cream, lotion, liquid or ointment. In an embodiment the medicament or pharmaceutical composition is a human medicament or pharmaceutical composition. In an embodiment the medicament or pharmaceutical composition is a veterinary medicament or pharmaceutical composition.

In an embodiment the composition comprising adipose tissue-derived secretions is of bovine origin. In an embodiment the composition comprising adipose tissue-derived secretions is of porcine origin.

In an embodiment the composition comprising adipose tissue-derived secretions further comprises adipocytes. In an embodiment the composition comprising adipose tissue-derived secretions is substantially free of adipocytes.

In an embodiment the composition comprising adipose tissue-derived secretions is prepared from a cell suspension comprising adipocytes. In an embodiment the composition comprising adipose tissue-derived secretions is prepared from a cell suspension substantially free of adipocytes.

In an embodiment the subject is a human. In embodiment the subject is an adolescent human. In an embodiment the subject is a non-human mammal. In an embodiment the non-human mammal is a canine. In an embodiment the non-human mammal is a feline. In an embodiment the non-human mammal is an equine. In an embodiment the non-human mammal is an ovine.

In an embodiment the adipose tissue-derived secretions is autologous to the subject. In an embodiment the adipose tissue-derived secretions is allogeneic to the subject. In an embodiment the adipose tissue-derived secretions is xenogeneic to the subject. In an embodiment the adipose tissue-derived secretions is of bovine origin. In an embodiment the adipose tissue-derived secretions is of porcine origin.

In an embodiment the adipose tissue-derived secretions or a cell culture comprising said secretions is concentrated, such as by freeze-drying and re-hydration in a suitable liquid and volume. In an embodiment the re-hydration is in a volume between about 5 and about 20 fold less than the original volume pre-freeze drying.

In an embodiment adipocytes are added to the adipose tissue-derived secretions.

In a seventh aspect there is provided a method for preparing bovine adipose tissue-derived secretions, the method comprising:
(i) exposing a sample of bovine adipose tissue to a proteolytic enzyme solution to generate a cell suspension;
(ii) centrifuging the suspension of cells to form a cell pellet, a free lipid layer above a floating cell layer which comprises adipocytes and an intermediate layer between the cell pellet and the floating cell layer, said intermediate layer being depleted of cells relative to the cell pellet and the floating cell layer; and
(iii) removing the free lipid layer and the intermediate layer,
(iv) optionally removing part or substantially all of the floating cell layer which comprises adipocytes,
(v) mixing the cell pellet and, if present, the floating cell layer comprising adipocytes to form an adipose tissue derived cell suspension which may or may not include adipocytes;
(vi) culturing the cell suspension under appropriate conditions;
(vii) harvesting supernatant of the cell culture to form a composition comprising bovine adipose tissue-derived secretions.

In an embodiment the proteolytic enzyme solution comprises collagenase at a final concentration of about 0.25% w/v. In an embodiment the digestion of the bovine adipose tissue is incomplete.

In an embodiment the floating cell layer comprising adipocytes is retained. In an embodiment the floating cell layer comprising adipocytes is partially removed. In an embodiment the floating cell layer comprising adipocytes is removed.

In an embodiment the step of culturing the cell suspension under appropriate conditions comprises culturing to form an adherent culture. In an embodiment the adherent cell culture is a confluent cell culture. In an embodiment the step of culturing the cell suspension under appropriate conditions comprises culturing cells in a spinner culture. In an embodiment the harvested supernatant further comprises adipocytes. In an embodiment the harvested supernatant is substantially free of adipocytes. In an embodiment the method further comprises a step of removing cells from said harvested supernatant.

In an embodiment the method further comprises freeze-drying the cell culture. In an embodiment the method further comprises freeze-drying the bovine adipose tissue-derived secretions. In an embodiment the freeze-dried material is re-hydrated in a suitable liquid at a suitable volume. In an embodiment the re-hydration is in a volume between about 5 and about 20 fold less than the original volume pre-freeze drying.

In an eighth aspect there is provided use of a composition comprising bovine adipose tissue-derived secretions for the manufacture of a medicament for topical use in (i) the treatment of a non-inflammatory condition in a subject, or (ii) stimulating hair, wool, or fur growth in a subject, or (iii) the treatment or prevention of acne in a subject.

In an embodiment the composition comprising bovine adipose tissue-derived secretions is prepared according to a method of the seventh aspect.

In a ninth aspect there is provided a pharmaceutical composition comprising bovine adipose tissue-derived secretions, together with a pharmaceutically-acceptable carrier or diluent.

In an embodiment the pharmaceutical composition or medicament is formulated for topical administration, such as in the form of a lotion, cream, liquid or ointment. In an embodiment the pharmaceutical composition or medicament is suitable for use on a human subject. In an embodiment the pharmaceutical composition or medicament is suitable for use on a non-human subject.

In an embodiment the composition comprising bovine adipose tissue-derived secretions further comprises adipocytes. In an embodiment the composition comprising bovine adipose tissue-derived secretions is substantially free of adipocytes.

The summary of the invention described above is not limiting and other features and advantages of the invention will be apparent from the following detailed description of the preferred embodiments, as well as from the claims.

BRIEF DESCRIPTION OF THE DRAWINGS

Preferred forms of the present invention will now be described with reference to the accompanying drawings in which:

FIG. 2: Trial results from seven human individuals topically administered a composition comprising bovine adipose tissue-derived secretions for the treatment of acne. (A) showing individual trial subject results and (B) showing results averaged per day over the seven individuals.

ABBREVIATIONS

Figure 1:
FIG. 1: Hair re-growth in shaved patches of a single dog, photographed at 7, 12 and 22 days after shaving. The left hand panels ("treated") show hair re-growth on the shaved patch to which bovine adipose tissue-derived secretions were topically administered twice a day whilst the right hand panels ("control") show hair re-growth on the shaved patch which received no treatment.

For convenience, the following abbreviations used in this specification are listed below.
DMEM Dulbecco's Modified Eagles Medium
RPMI Roswell Park Memorial Institute Medium
SVCs stromal vascular cells Definitions In the context of the present invention reference to a composition comprising "adipose tissue-derived secretions" will be understood to mean a composition which includes one or more factors released from cells of the adipose tissue. The material used in the preparation of the composition comprising the secretions may include adipocytes or may be substantially free of adipocytes.

The term "pharmaceutically acceptable carrier or diluent" as used herein is intended to encompass not only a carrier or diluent which is suitable for topical administration to a human subject, but also a carrier or diluent which is suitable for topical administration to a non-human mammalian subject. In particular embodiments, the carrier or diluent is suitable for administration to a non-human mammalian subject. In particular embodiments the carrier or diluent is suitable for administration to a human subject.

The terms "treating", "treatment", "therapy" and the like in the context of the present specification refer to the alleviation of the symptoms and/or the underlying cause of a non-inflammatory disorder or skin condition or acne. For brevity, these may variously be referred to herein collectively as "condition" or "disorder". In certain embodiments a treatment will slow, delay or halt the progression of a disorder or the symptoms of the disorder, or reverse the progression of the disorder, at least temporarily. Hence, in the context of this invention the word "treatment" or derivations thereof such as "treating" when used in relation to a therapeutic application includes all aspects of a therapy, such as the alleviation of pain associated with the condition being treated, alleviation of the severity of the condition being treated, improvement in one or more symptoms of the condition being treated, improvement in the overall well-being of the subject being treated, etc., such as in the treatment of acne an improvement in the appearance of the skin. Use of the word "treatment" or derivatives thereof will be understood to mean that the subject being "treated" may experience any one or more of the aforementioned benefits.

Throughout this specification, reference to "a" or "one" element does not exclude the plural, unless context determines otherwise.

The term "therapeutically effective amount" as used herein includes within its meaning a non-toxic but sufficient amount of a compound or composition for use in the invention to provide the desired therapeutic effect. The exact amount required will vary from subject to subject depending on factors such as the species being treated, the age and general condition of the subject, co-morbidities, the severity of the condition being treated, the particular agent being administered and the mode of administration and so forth. Thus, for any given case, an appropriate "effective amount" may be determined by one of ordinary skill in the art using only routine methods.

In the context of this specification, the term "comprising" means including, but not necessarily solely including. Furthermore, variations of the word "comprising", such as "comprise" and "comprises", have correspondingly varied meanings. Hence, the term "comprising" and variations thereof is used in an inclusive rather than exclusive meaning such that additional, integers or features may optionally be present in a composition, method, etc. that is described as comprising integer A, or comprising integer A and B, etc.

In the context of this specification the term "about" will be understood as indicating the usual tolerances that a skilled addressee would associate with the given value.

In the context of this specification, where a range is stated for a parameter it will be understood that the parameter includes all values within the stated range, inclusive of the stated endpoints of the range. For example, a range of "5 to 10" will be understood to include the values 5, 6, 7, 8, 9, and 10 as well as any sub-range within the stated range, such as to include the sub-range of 6 to 10, 7 to 10, 6 to 9, 7 to 9, etc, and inclusive of any value and range between the integers which is reasonable in the context of the range stated, such as 5.5, 6.5, 7.5, 5.5 to 8.5 and 6.5 to 9, etc.

In the context of this specification, the term "plurality" means any number greater than one.

It is to be noted that reference herein to use of the inventive methods and compositions in treatment or therapy will be understood to be applicable to human and non-human, such as veterinary, applications. Hence it will be understood that, except where otherwise indicated, reference to a patient, subject or individual means a human or a non-human, such as an individual of any species of social, economic or research importance including but not limited to members of the classifications of ovine, bovine, equine, porcine, feline, canine, primates, rodents, especially domesticated members of those classifications, such as sheep, cattle, horses and dogs.

To the extent that it is permitted, all references cited herein are incorporated by reference in their entirety.

DETAILED DESCRIPTION OF THE PREFERRED EMBODIMENTS

The present invention will now be described in more detail, including, by way of illustration only, with respect to the examples which follow.

Surprisingly, the inventors have identified that secretions from adipose tissue-derived cells which may or may not include adipocytes are effective for improving various non-inflammatory conditions, for stimulating the growth of hair, wool and fur, and for alleviating acne. Described herein are topical compositions comprising adipose tissue-derived secretions and use of these compositions for treating, non-inflammatory disorders, for the stimulation of hair, fur and wool growth and for the treatment or prevention of acne.

Accordingly, in an aspect of the present invention there is provided a method of treating a non-inflammatory disorder in a subject, the method comprising topically administering to the subject a pharmaceutical composition comprising adipose tissue-derived secretions together with a pharmaceutically-acceptable carrier or diluent.

The term "inflammatory" when used in reference to a disorder refers to a pathological process which is caused by, resulting from, or resulting in inflammation that is inappropriate or which does not resolve in the normal manner. Inflammatory disorders may be systemic or localized to particular tissues or organs. The non-inflammatory conditions contemplated for treatment in the present invention are conditions which do not arise as a result of inappropriate inflammation or inflammation that does not resolve in a normal manner.

Treatment of a non-inflammatory disorder includes the alleviation of one or more symptoms or manifestations of such a disorder. For example, the method of the invention includes treatment of a skin condition. In particular embodiments the present invention provides a method of treating a skin condition, wherein the skin condition is not a manifestation of an inflammatory disorder. Although a particular condition contemplated for treatment in this invention may manifest in a degree of inflammation, such as where the condition is sunburn, such conditions are not generally classified as inflammatory disorders and so are non-inflammatory conditions or manifestations of non-inflammatory conditions for the purposes of the present invention.

Specific conditions contemplated for treatment under the present invention include (i) dry skin, (ii) itchy skin, (iii) insect bite or sting, (iv) sun burn, (v) wrinkling of the skin, (vi) thin skin, (vii) cracking of the skin, (viii) acne, (ix) scarring, (x) stretch marks, (xi) sun spots, (xii) age spots, (xiii) liver spots, (xiv) puffiness and or dark circles around the eyes, (xv) athlete's foot, (xvi) warts, and said treatment alleviates one or more of said conditions.

A further surprising effect of the adipose tissue-derived secretions and pharmaceutical compositions thereof is that when administered to an individual they stimulate hair growth. In a further aspect of the invention therefore there is provided a method of stimulating hair, wool or fur growth in a subject, the method comprising topically administering to the subject a composition comprising adipose tissue-derived secretions, together with a pharmaceutically-acceptable carrier or diluent.

The composition is formulated for topical administration to the individual. In certain embodiments the subject is a human. The ability of the compositions to provide stimulation of hair growth in an individual is beneficial where the subject has one or more of (i) surgery-related hair loss, (ii) chemotherapy-related hair loss, (iii) radiation exposure-related hair loss, (iv) alopecia, (v) male pattern baldness, (vi) female pattern baldness.

In certain embodiments the subject to which the composition is to be administered is a non-human animal kept for the purpose of production of wool or fur. For example, the subject may be an ovine, particularly a sheep, kept for the production of wool. In certain embodiments the non-human mammal is a companion animal or show animal or stud animal, such as a canine, a feline, bovine or an equine.

Acne

The inventor has identified that the adipose tissue-derived secretions and pharmaceutical compositions thereof are effective in the treatment of acne. Acne typically occurs as a result of blockages in skin follicles, pores, or sebaceous glands, which may occur through the accumulation of dead skin cells and or sebum. This may be exacerbated by bacterial colonisation of the blocked follicle, pore or gland, such as by the naturally occurring commensal bacterium *Propionibacterium acnes* or by *Staphylococcus epidermidis*.

Acne typically affects areas of the skin in which sebaceous follicles or glands are denser, such as the face, the upper part of the chest and the back. In more severe cases of acne, the acne cysts may occur in areas of the skin where sweat collects in hair follicles and perspiration ducts, such as on the buttocks, groin and armpit area. Acne can manifest in non-inflammatory forms although severe acne may also have an inflammatory component. It will be understood that the acne contemplated for treatment or prevention in the present invention may have an inflammatory component. It will also be understood that the acne contemplated for treatment or prevention in the present invention may be non-inflammatory.

Acne occurs most commonly during adolescence and often continues into adulthood. In adolescence the occurrence of acne may be related to an increase in androgens, such as testosterone, the levels of which increase in males and females during puberty.

Physical manifestations of acne can be variable and range in severity of both appearance and long-term effect. Mild acne, for example, may include scaly red skin, blackheads and whiteheads (also referred to as comedones), papules (also referred to as pinheads), and in more severe cases pustules or pimples, nodules and cysts. Larger nodules have been referred to as nodulocystic acne or cystic acne. Cystic acne typically affects deeper skin tissue than does common acne. Aside from the physical discomfort and potential psychological effects of the presence of acne on the individual, the acne can have longer term effects on the individual, such as through physical scarring of the skin.

The invention contemplates the treatment or prevention of all forms of acne. In a specific embodiment the methods are directed at clinically relevant acne. As used herein, clinically relevant acne is acne which has the potential to detrimentally affect an individual, either physically, such as by scarring, or emotionally, to the extent that clinical intervention is advisable. Clinical intervention may or may not be by a trained physician. Typically, intervention would be advisable in subjects with moderate to severe acne, or in subjects with one or more large nodules or cysts, or in subjects with widespread acne, or in subjects with a personal or family history of moderate to severe acne.

Through the use of adipose tissue-derived secretions and pharmaceutical compositions thereof as described herein an individual with acne may experience improvement of the condition, including reduced inflammation of the affected area of the skin, accelerated healing and reduced scarring. As demonstrated herein, continued use of the composition of the invention may prevent the recurrence of acne in an individual or may reduce the severity of recurrent acne.

Adipose Tissue

Adipose tissue may be human adipose tissue or mammalian animal adipose tissue. The human or animal may be alive or dead, but preferably provided that there are still viable adipocyte cells within the adipose tissue. The adipose tissue may be derived from a mature animal or from a juvenile animal. In particular embodiments the animal is a companion animal, such as a canine or a feline domestic animal, or a working animal. In other particular embodiments the mammal is a farm animal, stud animal, or racing animal such as equines (including horses, donkeys, asses), bovines (including cattle and buffaloes), ovines, caprines, porcines, and camelids (including camels, llamas, alpacas and the like). In other embodiments the animal is a research animal, such as a rodent. In other embodiments the animal is a zoo animal, such as a member of the family Felidae, a member of the family Canidae, a member of the order Rodentia, or a member of the one of the orders of Cetacea, Perissodactyla, Artiodactyla, Tubulidentata, Hyracoidea, Sirenia, or Proboscidea. In preferred embodiments the adipose tissue is bovine or porcine.

The adipose tissue may originate from the same individual subject in which the pharmaceutical composition comprising adipose tissue-derived secretions will be administered, in which the adipose tissue and hence the adipose tissue-derived secretions is autologous. The adipose tissue may originate from a different individual of the same species to the subject in which the pharmaceutical composition comprising adipose tissue-derived secretions will be administered, in which the adipose tissue and hence the adipose tissue-derived secretions is allogeneic. In certain embodiments the adipose tissue may originate from an individual of a different species to the subject in which the pharmaceutical composition comprising adipose tissue-derived secretions will be administered, in which the adipose tissue and hence the adipose tissue-derived secretions is xenogeneic. The adipose tissue may originate from a single source or may originate from more than one source, such as more than one individual of a single species or from multiple species.

The adipose tissue may originate from any source in the body which is accessible. Subcutaneous fat, for example, is readily accessible with only superficial wounding, such as by excision from the tail base, or by using keyhole surgery techniques. Subcutaneous adipose tissue may be collected using liposuction techniques. Adipose tissue may, for example, be removed with reproductive tissue when de-sexing a male or female mammal. Adipose tissue may be removed froth a freshly killed animal. The adipose tissue may comprise "white" adipose tissue and/or "brown" adipose tissue. In particular embodiments the adipose tissue comprises white adipose tissue only.

The adipose tissue may be rinsed with a tissue culture medium or buffered isotonic solution to remove adherent red blood cells. The adipose tissue may also be rinsed with a disinfectant such as betadine and may be trimmed or coarsely processed to remove large blood vessels or connective tissue elements prior to generating an adipose tissue-derived cell suspension.

Adipose Tissue-Derived Cell Suspension

The adipose tissue-derived cell secretions and hence the compositions comprising such secretions, are preferably prepared by first obtaining or preparing an adipose tissue-derived cell suspension. The cell suspension may comprise adipocytes or may be substantially free of adipocytes. A cell suspension for the purposes of preparing adipose tissue-derived secretions will be understood herein as being substantially free of adipocytes if the cell suspension has been significantly depleted of adipocytes compared to the starting material, such as by removal of the adipocyte fraction after centrifugation. It will be understood that substantially free of adipocytes when used in relation to a cell suspension includes complete absence of adipocytes and also includes the situation where minimal retention of adipocytes in the material has occurred.

The term "adipose tissue-derived cell suspension" as used herein encompasses isolated cells from adipose tissue or small aggregates or pieces of adipose tissue, or a mixture of two or more of isolated cells, small aggregates and pieces of adipose tissue.

The cell suspension may be obtained by mechanically dissociating adipose tissue using techniques which are readily available in the art. Any suitable method for the mechanical dissociation of adipose tissue may be used, for example by mincing adipose tissue with blades, or with scissors, or by forcing adipose tissue through screens or meshes with a pore size sufficient to break the tissue into isolated cells and/or small pieces of adipose tissue. A combination of suitable techniques may be used. Small aggregates of adipose tissue may form when dissociated adipose-derived cells reassociate into larger assemblies, for example on standing in a medium. Small pieces or aggregates of adipose tissue may be less than ten millimeters in maximum diameter, less than five millimeters in maximum diameter, less than one millimeter in maximum diameter, less than 500 µm in maximum diameter or less than 250 µm in maximum diameter. In certain embodiments, a mechanical dissociation technique is used without using one or more proteolytic enzymes. The techniques employed in these embodiments may be used to rapidly generate an adipose tissue-derived cell suspension.

The adipose tissue-derived cell suspension may be filtered through a mesh or screen to remove cell aggregates or tissue pieces which are greater than the mesh or screen pore size.

In certain embodiments, proteolytic enzymes are used to promote the dissociation of adipose tissue into an adipose tissue-derived cell suspension. Enzymes which are suitable for such a use are well known in the art, and include but are not limited to trypsin, and collagenase. The proteolytic enzymes may be removed or inactivated before using the adipose tissue-derived cell suspension, particularly where these enzymes may not be compatible with a desired use of the cell suspension. In certain embodiments, proteolytic enzymes in combination with techniques for the mechanical dissociation of adipose tissue are used to generate an adipose tissue-derived cell suspension.

In particular embodiments the cell suspension may be suspended in a medium. The medium may be added to the adipose tissue before, during or after the dissociation of the adipose tissue. The medium may be a medium which is capable of maintaining adipose tissue cell survival for at least 24 hours under appropriate culture conditions, such as a tissue culture medium. The medium may be an isotonic buffered solution, such as a phosphate or a HEPES buffered saline, which is capable of maintaining adipose tissue cell survival for at least one hour. The medium may be a serum free medium. The medium may comprise serum or serum components which support or extend adipose tissue cell survival in the cell suspension. The serum or serum components may be autologous serum or serum components. The serum or serum components may be allogeneic serum or serum components from a single individual or pooled from multiple individuals.

In a further embodiment the cell suspension is not suspended in a medium, but instead the cells are suspended in liquid which is formed during the dissociation of the tissue.

In certain embodiments the preparation of an adipose tissue-derived cell suspension comprises a centrifugation step. The centrifugation of isolated cells or small aggregates or pieces of adipose tissue suspended in a liquid, such as a medium, is at approximately 500 g for 10 minutes, or for sufficient time and at a sufficient g-force to generate a cell pellet which comprises adipose-derived non-adipocyte cells, above which is a layer of medium, floating above which in turn is a layer which comprises adipocytes, and floating at the top is a layer of lipid which is derived from ruptured adipocytes.

Following centrifugation, in certain embodiments the medium layer, which comprises secretions from adipocytes, may be collected, thereby representing one composition or source of adipose tissue-derived secretions. In this embodiment the collected medium or composition comprising secretions may or may not comprise adipocytes.

In certain other embodiments, following centrifugation the lipid layer and the medium layer will be discarded and the retained cells are mixed, leaving an adipose tissue-derived cell suspension which comprises adipocytes and adipose-derived non-adipocyte cells.

In certain other embodiments, following centrifugation the lipid layer, the medium layer, and the floating layer which comprises adipocytes will be discarded, thereby retaining primarily adipose-derived non-adipocyte cells.

In certain embodiments multiple centrifugation steps may be used, for example to provide additional cell separation steps.

In other embodiments, the preparation of an adipose tissue-derived cell suspension does not include a centrifugation step.

The adipose tissue-derived cell suspension may be freshly isolated, that is it may be utilised for the preparation of adipose tissue-derived secretions which will be administered to the recipient within approximately 6 hours of the removal of the fat tissue from the donor. In these embodiments, the preparation of the adipose tissue-derived secretions typically does not include a step of culturing the cells as described herein. Alternatively, the adipose tissue-derived cell suspension may be stored for more than 6 hours, typically when suspended in a medium, prior to being utilised for the preparation of adipose tissue-derived secretions.

The adipose tissue-derived cell suspension utilised for the preparation of adipose tissue-derived secretions may or may not comprise adipocytes. In particular embodiments the adipocytes comprise viable adipocytes. In particular embodiments, the adipocytes retain detectable quantities of lipid in their cytoplasm, and may be separated from adipose-derived non-adipocyte cells on the basis of the different density provided by the lipid. Lipid may be detectable using light microscopy techniques, including phase contrast microscopy, or by staining a sample of cells with a lipophilic dye such as Oil Red O. Adipocytes which retain lipid in their cytoplasm are considerably more fragile than other adipose-derived cells and accordingly, where viable adipocytes are required, techniques for dissociating tissue which damage or render non-viable a large proportion of the adipocytes should be avoided. The ultrasonic dissociation of adipose tissue or techniques in which adipose tissue is vigorously shaken, for example, are unlikely to provide a cell suspension which contains large numbers, of viable adipocytes. The viability of adipocytes may readily be determined using readily available techniques, such as the LIVE/DEAD cell viability assays (Life Technologies).

In certain embodiments, the adipose tissue-derived cell suspension does not comprise substantial numbers of adipose-derived non-adipocyte cells. In these embodiments, the adipose tissue-derived cell suspension may be conveniently prepared by methods which comprise a centrifugation step, as described herein, by which the pelleted adipose-derived non-adipocyte cells are excluded.

In certain embodiments, the adipose tissue-derived cell suspension comprises both adipocytes and adipose-derived non-adipocyte cells. In these embodiments, the adipose tissue-derived cell suspension may be conveniently prepared by methods which comprise a centrifugation step, as described herein, in which both the adipocyte cell layer and the pelleted adipose-derived non-adipocyte cells are collected. Alternatively, in these embodiments the adipose tissue-derived cell suspension may be prepared by dissociating adipose tissue as described herein without a centrifugation step.

Bovine Adipose Tissue Derived Cell Suspensions

The inventors have surprisingly found that the preparation of adipose tissue derived cell suspensions from bovine sources, particularly from bovine tail base tissue, is refractory to standard methods appropriate to multiple other sources of adipose tissue, such as human, canine, equine, mouse and rat. Accordingly, the application of the present invention, in so far as it utilises bovine adipose-derived cell secretions, optimally also employs a method for preparing, a bovine adipose tissue-derived cell suspension, the method comprising:

exposing a sample of bovine adipose tissue to a proteolytic enzyme solution to generate a cell suspension;

centrifuging the suspension of cells to form a cell pellet, a free lipid layer above a floating cell layer which comprises adipocytes and an intermediate layer between the cell pellet and the floating cell layer, said intermediate layer being depleted of cells relative to the cell pellet and the floating cell layer; and removing the free lipid layer and the intermediate layer optionally removing part or substantially all of the floating cell layer which comprises adipocytes, mixing the cell pellet and, if present, the floating cell layer to form an adipose tissue derived cell suspension which may or may not include adipocytes.

As described herein the adipocyte layer, also referred to as the floating cell layer, may or may not be removed during the processing. The methods and compositions of the invention therefore include, in various embodiments, the optional removal of the adipocyte layer leading to a cell suspension that is substantially depleted of adipocytes; the optional retention of the adipocyte layer leading to a cell suspension that includes adipocytes; the optional partial removal of the adipocyte layer.

In certain embodiments the method may comprise additional steps in the preparation of adipose tissue-derived cell suspensions as set out elsewhere in this specification, in particular the previous section headed "Adipose Tissue-Derived Cell Suspension". These additional steps include, for example, mechanically dissociating the tissue, and suspension via a medium or buffer etc.

The removed intermediate layer may be retained as it typically includes adipose tissue-derived secretions.

In certain embodiments the proteolytic enzyme solution comprises collagenase.

In certain embodiments the collagenase is used at a final concentration of about 0.25% w/v or greater. In certain embodiments the exposure of the bovine adipose tissue to proteolytic enzyme is conducted under conditions which result in incomplete digestion of the adipose tissue, such as which result in significant amounts of intact adipose tissue being present. Typically, for example, there may be pieces of adipose tissue present that are the same size as they were prior to starting the digestion. In embodiments of the method anywhere between about 20% to about 80% of the adipose tissue may not be digested.

In certain embodiments the cells may be subjected to multiple centrifugation steps or wash steps, for example in order to remove excessive free lipid.

As described further in the following section an adipose tissue-derived cell suspension which may be of any species origin, such as mentioned herein, for example bovine, porcine, canine, feline, human, etc, or an aliquot thereof, may be used in the preparation of a composition comprising secretions of the adipose tissue-derived cells.

Compositions Comprising Adipose Tissue-Derived Secretions

A composition comprising secretions from the adipose tissue-derived cells may be prepared from an adipose tissue-derived cell suspension, which may or may not comprise adipocytes, by any appropriate manner. As noted herein the liquid components formed during the preparation of an adipose tissue-derived cell suspension typically includes adipose tissue-derived secretions, thereby representing one embodiment of a composition comprising such secretions. In this form the composition comprising adipose tissue-derived secretions may be collected at any appropriate stage in the preparation of a cell suspension, such as by collection of the intermediate liquid layer between the cell pellet and the floating cell layer after centrifugation of the adipose tissue-derived material. In this embodiment the collected material comprising secretions may or may not include adipocytes.

Typically, the composition is generated by exposure of a medium to the adipose tissue-derived cell suspension. Exposure of the medium to the adipocyte tissue-derived cell suspension does not require conditions which enable cell attachment to a substratum. In these embodiments, the composition comprising adipose tissue-derived secretions may be generated by exposing a medium to the adipose tissue-derived cell suspension for any appropriate period of time, such as at least 6 hours, at least 8 hours, at least 10 hours, or at least 12 hours, followed by removal of the cell suspension from the medium, or vice versa, for example by centrifugation or by filtration. The removal of the cell suspension and the medium from each other may result in complete or incomplete removal of cells. Hence the medium, which comprises the adipose tissue-derived secretions, may or may not include adipocytes after removal from the cell suspension. In certain embodiments the composition is generated by exposing a medium to the adipose tissue-derived cell suspension for no more than 12 hours, no more than 18 hours or no more than 24 hours. The composition may comprise cell-derived molecules which are released from cells following cell death or the breakup of adipose tissue cells. The composition comprises secretions of cells of the adipose tissue-derived cell suspension. The exposing of a medium to an adipose tissue-derived cell suspension may be at a temperature of from 4° C. to 50° C., more typically at a temperature of from 10° C. to 40° C. and most typically at a temperature of from 20° C. to 37° C.

For a typical adipose tissue-derived cell suspension, 5 g of adipose tissue is dissociated and suspended in 50 mls of DMEM containing 10% autologous serum. The adipose tissue derived cell suspension typically comprises from 100,000 to 1,000,000 non-adipocyte cells for every gram of adipose tissue source material. The number of adipocytes per gram of adipose tissue source material is typically between 100,000 and 5,000,000.

The term "medium" as used herein is intended to encompass compositions which support the survival of at least some cells in an adipose tissue-derived cell suspension for at least one hour. The medium may be a tissue culture medium, such as DMEM, RPMI, or minimal essential medium, optionally supplemented with serum. The medium may be a buffered isotonic solution, such as a phosphate buffered saline or Hank's buffered saline solution, provided the medium is suitable for administration to a subject. The medium may be liquid which is formed during the dissociation of adipose tissue. The medium may optionally be supplemented with factors which promote cell survival or attachment and cell division, such as insulin, progesterone and selenium, or serum or serum components. In certain embodiments the medium must be suitable for a pharmaceutical composition, which is acceptable for in vivo use. Such media will be substantially free of pyrogens or other impurities which may be harmful to humans or animals. Pharmaceutically-acceptable media are commercially available. The phrase "pharmaceutically acceptable" refers to molecular entities and compositions that do not produce adverse, allergic, or other untoward reactions when administered to an animal or a human.

Preparation of a composition comprising adipose tissue-derived secretions may include a step of lysis of the adipose tissue-derived cell suspension. A lysate comprising cell secretions may be prepared by any suitable method. In an example embodiment, an adipose tissue-derived cell suspension may be exposed to a medium, such as described above. Cells of the suspension may then be lysed by any suitable means, such as by mechanical disruption (eg, vigorous shaking or agitation), ultrasonic disruption, freeze thawing, freeze drying or the addition of one or more agents capable of inducing cell lysis, such as adipocyte lysis. Such lysing agents are known in the art and include urea, sodium dodecyl sulphate and Triton x100. After a lysis step the preparation may be centrifuged or filtered to assist in the removal of cell debris, or it may be used without such a clarifying step, in which case the composition comprising adipose tissue-derived secretions may also include cell debris. In some cases the cell lysate may be removed from the lysing agent by precipitation of the cell lysate. Where the lysis step results in incomplete cell lysis, the composition comprising adipose tissue-derived secretions may also comprise adipose-derived cells, such as adipocytes.

In certain embodiments preparation of the adipose tissue-derived secretions comprises culturing the cell suspension under appropriate conditions. Methods for culturing a cell suspension are known in the art and include, for example, culturing the cells to form an adherent cell culture, such as a confluent adherent cell culture, and culturing the cells in a spinner culture. At any appropriate time during, or after, culturing of the cells supernatant is harvested, such as from an adherent cell culture, which may be a confluent adherent cell culture, and optionally, removing cells from said supernatant to form a composition comprising adipose tissue-derived secretions. The cell suspension so-cultured may comprise adipocytes or may be substantially free of adipocytes. The removal of the cells from the supernatant to leave a composition comprising adipose tissue-derived secretions may be complete removal or may be partial removal. In the latter case, the composition comprising adipose tissue-derived secretions may therefore also include adipocytes.

Prior to commencing the culturing of the cells, the adipose tissue derived cell suspension may be re-suspended in a desired volume of an appropriate buffer, such as DMEM, RPMI or minimal essential media. The cell suspension, or an aliquot thereof, may be added to a sterile tissue culture flask and incubated under appropriate conditions, typically until the adherent cells have reached confluence. The cell culture is preferably in the presence of sterile serum. The concentration of the serum in the culture may be any suitable concentration which assists culturing of adipose tissue-derived cells, such as for example in the range of about 1% v/v to about 30% v/v, such as about 10% v/v, or about 15% v/v or about 20% v/v. The serum may be any appropriate serum for the culturing of adipose tissue-derived cells, such as a commercial fetal calf serum, or a serum prepared in house, such as by methods known in the art. Preferably the serum is autologous, having been prepared from the same individual from which the adipose tissue was obtained, or allogeneic. Typically, the cells are cultured at 37° C. with 5% $CO_2$.

During culturing the adipose tissue-derived cells secrete cytokines including anti-inflammatory molecules, pro-inflammatory molecules, growth factors and other cell signalling molecules into the medium. The supernatant in the culture thereby comprises adipose tissue-derived secretions.

In certain embodiments the culture may be frozen and freeze dried, resulting in a freeze dried preparation that includes cells and the secretions. Rehydration of the freeze dried preparation will lyse the majority of the cells resulting in the release of additional cytokines. Rehydration will typically be performed using a volume of fluid that is less than the original volume of the adipose tissue-derived cells, such as a volume of fluid that is between about 5 and about 20 times less than the original volume, more typically about 10 times less than the original volume of the adipose tissue-derived cells which results in a composition that is 10 times concentrated. The composition may then be filtered to remove cell debris resulting in a composition that contains concentrated cytokines. This provides a preferred method for producing large volumes of concentrated secretions.

In other certain embodiments the supernatant may be harvested from the culture at any appropriate time, although typically for an adherent cell culture it will be harvested when the cells have reached confluence, such as after about 3, 4, 5, 6, 7, 8, 9, 10, 11, 12, 13 or 14 days. Cells, cell debris and any remaining adipose tissue may be removed from the supernatant, such as by filtration. In an embodiment the filtration may be through a 20 micron mesh. If desired, multiple steps of filtration may be undertaken such as through two or more filters of decreasing mesh size. The resultant preparation of adipose tissue-derived secretions is typically filter sterilised, such as through a 0.22 micron filter. The sterilised composition may be used immediately, or may be aliquoted for use, or for storage. Typically, if stored, the composition is stored frozen at −20° C. The composition contains secretions from the adipose tissue-derived cells.

A composition comprising adipose tissue-derived secretions may also comprise adipocytes. Where present, the adipocytes may remain from the original adipose tissue used in the preparation of the secretions or they may be added to the composition comprising the secretions.

Pharmaceutical Compositions and Other Compositions of the Invention

In aspects of the invention the adipose tissue-derived composition, containing secretions of adipose tissue cells, is used for the preparation of a pharmaceutical composition for topical use. According to one aspect the invention provides a composition comprising adipose tissue-derived secretions for the preparation of a pharmaceutical composition for topical use in the treatment of a non-inflammatory disorder in a subject. In another aspect the invention provides a composition comprising adipose tissue-derived secretions for the preparation of a pharmaceutical composition for topical use for stimulating hair, wool or fur growth in a subject. In another aspect the invention provides a composition comprising adipose tissue-derived secretions for the preparation of a pharmaceutical composition for topical use for the treatment or prevention of acne, or one or more symptoms thereof. Typically the pharmaceutical composition also comprises one or more of a pharmaceutically acceptable carrier diluent, excipient or adjuvant. According to a further aspect the invention provides a pharmaceutical composition comprising adipose tissue-derived secretions, together with a pharmaceutically acceptable carrier, diluent, excipient or adjuvant. In certain embodiments the composition comprising adipose tissue-derived secretions further comprises adipocytes.

In certain embodiments, the adipose tissue is taken from an individual subject, and the pharmaceutical composition is topically administered to the same individual, and thus the adipose tissue-derived secretions is a purely autologous preparation.

In certain embodiments, the adipose tissue is taken from one or more individual subjects and the pharmaceutical composition is topically administered to a different subject of the same species, and thus the adipose tissue-derived secretions is an allogeneic cell suspension. In certain embodiments the adipose tissue is taken from an individual of a different species to that which is intended to be a recipient of the adipose tissue-derived secretions. For example, a composition comprising secretions prepared from bovine or porcine tissue may be intended for topical administration to an individual of a different species, such as a human. In embodiments where the composition comprising adipose tissue-derived secretions is for use in a different individual of the same species as the source material or for use in an individual of a different species as the source material, the composition may typically be devoid of cells of the immune system in order to minimise the possibility of host (recipient) immune response to the composition or graft versus host disease.

In certain embodiments the pharmaceutical composition is prepared from more than one source of adipose tissue, such as from different preparations taken from the same individual or from different preparations taken from different individuals. The pooling may comprise combining multiple adipose tissue-derived cell suspensions, such as in a pooled culturing step or the pooling may comprise combining multiple compositions of adipose tissue-derived secretions, such as may be obtained from separate culturing or exposure steps.

The pharmaceutical composition is topically administered to the subject, typically by direct or indirect contact with the skin. Topical administration used herein will also be understood to include transdermal delivery. Typically a transdermal delivery system will comprise the pharmaceutical composition formulated with one or more agents which increase the permeability of the skin to the composition.

The pharmaceutical composition for topical administration, for example for the treatment of skin conditions or for the stimulation of hair growth, or for the treatment or prevention of acne, may be formulated in an aqueous based cream or lotion, such as a cetomacrogol cream or a sorbolene cream, to increase residency at the skin surface. As described herein the inventors have identified that the compositions of the invention are effective in stimulating hair, fur or wool growth. Accordingly, the compositions of the invention for topical use include products routinely used in hair care such as shampoos, conditioners, hair gels, and the like.

Where the pharmaceutical composition is administered to the cornea, it may be formulated with an oil-based ointment which is acceptable for corneal administration, or it may be admixed with corneally-acceptable artificial tear solutions which increase residency time at the corneal surface.

The invention will now be described in more detail, by way of illustration only, with respect to the following examples. The examples are intended to serve to illustrate this invention and should not be construed as limiting the generality of the disclosure of the description throughout this specification.

Example 1. Preparation of a Mixture of Adipocytes and Adipose-Derived Non-Adipocyte Cells A 10 g sample of adipose tissue was collected by excision from the groin of an adult dog. The adipose tissue was rinsed with saline and then minced finely using scissors and mixed with 20 ml of Dulbecco's Modified Eagle's Medium (DMEM, Sigma). Collagenase (Sigma) was added to achieve a final concentration of 0.05% w/v and the sample was incubated at 37° C. for 90 minutes. During the incubation the sample was gently inverted by hand every 15 minutes.

Following collagenase treatment the sample was aseptically filtered through a stainless steel mesh (300 μm pore size), transferred to a 50 ml centrifuge tube and centrifuged at 500 g for 15 minutes.

Four distinct layers were visible within the centrifuged sample: a small (2 mm thick) layer of free lipid on the surface, below which was a white 10 mm thick layer of adipocytes and then a large clear layer of liquid which largely comprised DMEM and then a pellet of adipose-derived non-adipocyte cells. The small layer of lipid was carefully removed with a pasteur pipette. A fresh pasteur pipette was then carefully inserted through the adipocytes and the clear DMEM was removed without disturbing the floating adipocytes or the pelleted cells. This resulted in a sample that contained only the floating adipocytes and the pelleted cells. The floating adipocyte's and the pelleted cells were gently mixed with a pasteur pipette and transferred to a 15 ml centrifuge tube.

The cells were then washed in DMEM to remove collagenase. DMEM was added to a final volume of 14 ml and the sample centrifuged at 500 g for 10 minutes. This resulted in three distinct layers: floating adipocytes, DMEM and pelleted adipose-derived non-adipocyte cells. The DMEM was carefully removed by inserting a pasteur pipette through the adipocytes taking care not to disturb the adipocytes or the pelleted cells.

The floating and the pelleted cells were gently resuspended in 4 ml of DMEM and mixed with a pasteur pipette.

Example 2. Preparation of a Cell-Free Extract from an Adipose Tissue-Derived Cell Suspension A 10 g sample of canine adipose tissue was minced finely using scissors and then mixed with 5 ml of DMEM. Autologous canine serum was filter sterilised and a 1 ml volume added to the mixture of minced tissue.

The tissue mixture was incubated at 37° C. overnight without agitation. The sample was then centrifuged at 1500 g for 15 minutes and the liquid between the floating layer of adipocytes and tissue and the pellet of adipose tissue-derived non-adipocyte cells was carefully harvested. The cell-free extract comprises secretions from the adipose tissue.

Example 3. Alternative Preparation of a Cell-Free Extract from an Adipose Tissue-Derived Cell Suspension A 10 g sample of adipose tissue was collected by excision from the tail-base of a horse. The adipose tissue was rinsed with saline and then minced roughly using scissors into pieces of approximately 5 mm diameter and mixed with 20 ml of Dulbecco's Modified Eagle's Medium (DMEM, Sigma). Collagenase (Sigma) was added to produce a final concentration of 0.05% [w/v] and the sample was incubated at 37° C. for 30 minutes. At the end of 30 minutes the adipose tissue was partially digested and consisted of a mixture of partially digested fat particles, liberated stromal vascular cells (SVCs) and liberated adipocytes.

The sample was then washed to remove collagenase by centrifuging at 500 g for 15 minutes. Four distinct layers were visible within the centrifuged sample: a small (2 mm thick) layer of free lipid on the surface, below which was a white 20 mm thick layer of adipose tissue and adipocytes and then a large clear layer of DMEM/collagenase and then a pellet of adipose tissue-derived non-adipocyte cells. The small layer of lipid was carefully removed with a pasteur pipette. A fresh pasteur pipette was then carefully inserted through the adipocytes and the clear DMEM was removed without disturbing the floating adipose tissue, adipocytes or the pelleted cells. This resulted in a sample that contained only the floating pieces of adipose tissue and adipocytes suspended in a small volume of DMEM and the pelleted cells. The pieces of adipose tissue and adipocytes and the pelleted cells were gently mixed with a pasteur pipette and transferred to a 15 ml centrifuge tube.

The pieces of adipose tissue and cells were then washed in DMEM to remove collagenase as follows, DMEM was added to a final volume of 14 ml and the sample centrifuged at 500 g for 10 minutes. This resulted in three distinct layers: floating pieces of adipose tissue and adipocytes, DMEM and pelleted adipose tissue-derived non-adipocyte cells. The DMEM was carefully removed by inserting a pasteur pipette through the adipocytes taking care not to disturb the pieces of adipose tissue, adipocytes or the pelleted cells.

Tissue Culture

The floating and the pelleted cells were gently resuspended in 10 ml of DMEM and transferred to a 300 ml tissue culture flask. A 30 ml volume of DMEM and 10 mls of autologous sterile serum were added and the flask was then incubated at 37° C. with 5% $CO_2$. The flask was examined daily by microscopy. Cells became attached and fibroblast-like in appearance between days 3 and 6.

Harvesting Cell Free Cell Secretions

After 6 days the supernatant was harvested and the suspended adipose tissue and cells were removed by filtration through a 20 micron mesh. The solution was filter sterilised through a 0.22 micron filter and then aseptically dispensed into 10 ml vials and stored frozen at −20° C.

Example 4. Production of a Mixture of Adipocytes and Adipose-Derived Non-Adipocyte Cells Depleted of Adherent Cells A 4 ml volume of adipocytes and adipose-derived non-adipocyte cells was prepared as described in Example 1. Autologous canine serum was filter sterilized and a 1 ml volume added to the cell mixture.

The cell mixture was incubated at 37° C. overnight in a tissue culture flask without agitation. The sample was examined using an inverted microscope and a layer of cells adhering to the surface of the flask was observed. Unattached cells and floating adipocytes were also observed. The non-adherent cells, comprising adipocytes and adipose-derived non-adipocyte cells were carefully tipped off and collected. These cells are suitable for the generation of a composition comprising adipose tissue-derived secretions.

Example 5. Preparation of a Suspension of Adipocytes

A 10 g sample of adipose tissue was collected by excision from the groin of a dog. The adipose tissue was rinsed with saline and then minced finely using scissors and mixed with 20 ml of Dulbecco's Modified Eagle's Medium (DMEM, Sigma). Collagenase (Sigma) was added to a final concentration of 0.05% v/v and the sample was incubated at 37° C. for 90 minutes. The sample was gently inverted by hand every 15 minutes.

The sample was then aseptically filtered through a stainless steel mesh (300 μm pore size), transferred to a 50 ml centrifuge tube and centrifuged at 500 g for 15 minutes.

Four distinct layers were visible within the centrifuged sample: a small (2 mm thick) layer of free lipid on the surface, below which was a white 10 mm thick layer of adipocytes and then a large clear layer of DMEM and then a pellet of adipose-derived non-adipocyte cells. The small layer of lipid was carefully removed with a pasteur pipette. A fresh pasteur pipette was then carefully inserted through the adipocytes and the clear DMEM and the pelleted cells were removed. This resulted in a sample that contained only the floating adipocytes. The adipocytes were gently mixed with a pasteur pipette and transferred to a 15 ml centrifuge tube.

The adipocytes were then washed in DMEM to remove collagenase as follows. DMEM was added to a final volume of 14 mls and the sample centrifuged at 500 g for 10 minutes. The DMEM was carefully removed by inserting a pasteur pipette through the adipocytes.

The floating cells, comprising adipocytes, were gently resuspended in 4 mls of DMEM. At each step the DMEM exposed to the adipose tissue or adipocytes will comprise adipose tissue-derived cell secretions.

Example 6. Preparation of Bovine Adipose Tissue-Derived Cell Suspensions

Adipose tissue from human, canine, domestic cats, snow leopard, equine, rat and mouse have all been digested with normal concentrations (0.02% or 0.05%) of collagenase. The use of standard methods for preparation of adipose tissue derived cells (mincing and collagenase digestion), such as those described above, were unsuccessful when applied to bovine tissue. The inventor initially attempted digesting with 0.02% v/v collagenase, this being the concentration that can be used successfully for human, canine and equine adipose tissue. This did not work. The digestion time was increased and shaking of the digestion mixture was introduced. This resulted in the minced tissue forming into one round solid lump. The collagenase concentration was increased to 0.1% and still the tissue did not digest. Surprisingly, it was not until a concentration of 0.25% v/v collagenase was used and the mixture was digested for two hours, that the tissue would digest.

Bovine adipose tissue is an attractive source of secretions due to its ready availability, the lack of zoonotic diseases (particularly in Australia) and acceptance by the public of using bovine products. For similar reasons the inventor considers that porcine adipose tissue is also an attractive source for use in methods of the invention.

Example 7. Production of Secretions from Bovine Adipose Tissue

Preparation of Adipose Tissue

A 10 g sample of adipose tissue was collected by excision from the tail-base of a two year old steer. The adipose tissue was rinsed with saline and then minced finely using scissors and mixed with 20 ml of Dulbecco's Modified Eagle's Medium (DMEM, Sigma). Collagenase (Sigma) was added to produce a final concentration of 0.25% [w/v] and the sample was incubated at 37° C. for 120 minutes.

The sample was then centrifuged at 500 g for 15 minutes. Four distinct layers were visible within the centrifuged sample: a small (2 mm thick) layer of free lipid on the surface, below which was a white 20 mm thick layer of adipose tissue and adipocytes and then a large clear layer of DMEM and then a pellet of adipose tissue-derived non-adipocyte cells. The small layer of lipid was carefully removed with a pasteur pipette. A fresh pasteur pipette was then carefully inserted through the adipocytes and the clear DMEM was removed without disturbing the floating adipose tissue, adipocytes or the pelleted cells. This resulted in a sample that contained only the floating pieces of adipose tissue and adipocytes suspended in a small volume of DMEM and the pelleted cells. The pieces of adipose tissue and adipocytes and the pelleted cells were gently mixed with a pasteur pipette and transferred to a 15 ml centrifuge tube.

The pieces of adipose tissue and cells were then washed in DMEM to remove collagenase as follows. DMEM was added to a final volume of 14 ml and the sample centrifuged at 500 g for 10 minutes. This resulted in three distinct layers: floating pieces of adipose tissue and adipocytes, DMEM and pelleted adipose tissue-derived non-adipocyte cells. The DMEM was carefully removed by inserting a pasteur pipette through the adipocytes taking care not to disturb the pieces of adipose tissue, adipocytes or the pelleted cells.

Tissue Culture

The floating and the pelleted cells were gently resuspended in 10 ml of DMEM and transferred to a 300 ml tissue culture flask. A 30 ml volume of DMEM and 10 mls of autologous sterile serum were added and the flask was then incubated at 37° C. with 5% $CO_2$. The flask was examined daily by microscopy. Cells became attached and fibroblast-like in appearance between days 3 and 6. The attached cells became confluent between days 5 and 10.

Harvesting Compositions Comprising Cell Secretions

Once cells were confluent on the base of the flask the supernatant was harvested and the suspended adipose tissue and cells were removed by filtration through a 20 micron mesh. The solution was filter sterilised through a 0.22 micron filter and then aseptically dispensed into 10 ml vials and stored frozen at −20° C.

Example 8. Production of Concentrated Secretions from Bovine Adipose Tissue

Bovine adipose tissue was collected, processed and placed into tissue culture flasks as described in Example 7.

Once the adherent cells became confluent the tissue culture flasks were frozen and then freeze dried in a Telstar Lyobeta freeze dryer for 2 days. The resulting freeze dried cake was rehydrated with 2.5 ml of distilled water. The concentrated sample was then desalted by passing through a PD10 column (GE Lifesciences). A 3.5 ml volume was eluted from the column. This small volume contained a concentrated mix of cytokines.

Example 9. Production of Secretions from Bovine Adipose Derived Cells Depleted of Adipocytes Preparation of Adipose Tissue A 10 g sample of adipose tissue was collected by excision from the tail-base of a two year old steer. The adipose tissue was rinsed with saline and then minced finely using scissors and mixed with 20 ml of Dulbecco's Modified Eagle's Medium (DMEM, Sigma). Collagenase (Sigma) was added to produce a final concentration of 0.25% [w/v] and the sample was incubated at 37° C. for 180 minutes.

The sample was then centrifuged at 500 g for 15 minutes. Four distinct layers were visible within the centrifuged sample: a small (2 mm thick) layer of free lipid on the surface, below which was a white 20 mm thick layer of adipose tissue and adipocytes and then a large clear layer of DMEM and then a pellet of adipose tissue-derived non-adipocyte cells. All the liquid and the floating layers were discarded.

The cells were then washed in DMEM to remove collagenase as follows. DMEM was added to a final volume of 14 ml, the sample centrifuged at 500 g for 10 minutes and then the DMEM was tipped off.

Tissue Culture

The pelleted cells were gently resuspended in 10 ml of DMEM and transferred to a 300 ml tissue culture flask. A 30 ml volume of DMEM and 10 mls of autologous sterile serum were added and the flask was then incubated at 37° C. with 5% $CO_2$. The flask was examined daily by microscopy. Cells became attached and fibroblast-like in appearance between days 3 and 6. The attached cells became confluent between days 5 and 10.

Harvesting Compositions Comprising Cell Secretions

Once cells were confluent on the base of the flask the supernatant was harvested and the cells were removed by filtration through a 20 micron mesh. The solution was filter sterilised through a 0.22 micron filter and then aseptically dispensed into 10 ml vials and stored frozen at −20° C.

Example 10

Examples 1-9 herein describe, inter alia, the preparation of adipose tissue-derived cell suspensions, wherein the suspension may or may not include adipocytes, and of cell free extracts comprising secretions from the adipose tissue (eg., Example 2). In the course of preparation of those cell suspensions the methods may comprise exposure of the adipose tissue, which may or may not be partially or completely digested, to a liquid, typically DMEM in the Examples. During that exposure the adipose tissue-derived cells including adipocytes secrete factors into the liquid. In the course of preparing an adipose tissue-derived cell suspension the liquid phase, such as DMEM, may be described as a composition comprising adipose tissue-derived secretions.

The adipose tissue-derived cell suspensions described in Examples 1-9 may be further utilized in the preparation of a composition comprising adipose tissue-derived secretions, such as by methods described herein. For example, the adipose tissue-derived cell suspensions may be exposed to a suitable medium and the medium collected, or the cell suspension may be lysed and the medium collected, or the cell suspension may be cultured under suitable conditions and the medium collected, or the cell suspension may be cultured and subjected to freeze drying followed by rehydration in a suitable liquid at a desired volume. Various examples for these methods of utilizing the adipose tissue-derived cells or cell suspensions in the preparation of a composition comprising adipose tissue-derived secretions are described herein.

Example 10. Acceleration of Hair Growth in Canines

Administration of adipose tissue-derived secretions to canines has resulted in acceleration of hair regrowth in the animals. Two related Ridgebacks had patches shaved on their shoulders. One dog had bovine secretions produced as described in Example 7 applied topically to the left patch, twice a day while the right patch received no treatment. The other dog had one patch shaved and received no treatment. The patches were photographed regularly. By two weeks the treated patch had grown back to 75% of original hair (FIG. 1 left hand panels). The untreated patch on the same dog was at approximately 20% regrowth (FIG. 1 right hand panels). The patch on the untreated dog was at 5% regrowth (not shown).

Example 11. Treatment of Skin Conditions in Humans

Secretions from bovine adipose tissue were prepared as described in Example 7. The secretions were mixed with an equal amount of Aqueous Base Cream BP and dispensed into plastic pots and stored at 4° C. until used. Pots of cream were provided to people for trialing for a range of topical applications. The following descriptions exemplify the manner in which the compositions were used by the various patients, the condition being treated and the outcomes, as described by the patients.

(i) Patient 1

Thank you for the opportunity to trial the cream. I applied the cream to two areas.

1. Scar on Face—(two year old scar)
2. Plantar Wart—(at least 5 years old)

1. Scar on Face

Commenced Trial: November 2010

I applied the cream daily directly on the scar.

The first week—no noticeable improvement.

The second week—scar looking less raised.

The third week—continued looking less raised/slightly faded.

The fourth week—till January 2011—no further improvement.

2. Plantar Wart

Commenced Trial: November 2010

I applied the cream directly on the plantar wart nightly.

The first four weeks—no noticeable improvement.

The fourth week—noticeable changes in the look of the wart.

The fourth week to January 11—daily improvements—leading to the wart disappearing completely.

(ii) Patient 2

I tried the cream on a surgical scar on my arm. It was applied to half the scar twice daily for around 3 weeks and there was an observable difference in the healing of the scar compared to the half not treated.

The half of the scar treated displayed a lighter and more consistent colour than the deeper crimson of the untreated section. Changes were noticed a few days after treatment.

(iii) Patient 3

The bovine secretions cream had a rapid and positive effect on sunburn.

The burn was moderate (significant skin redness and pain) on the face, forearms and shins. Cream was applied to the face and forearms twice in the evening after the sun exposure (approximately 1.5 hours and 5 hours after sun exposure). The second application of cream was immediately prior to bed. The skin was washed with water, but no soaps or non-soap cleansers were used.

No cream of any sort was applied to the skin on the burnt shins.

The burns on the arms and face was significantly less painful within 2 hours after the first application. By the following morning (after two applications) the face and arms were almost pain free. There was little pain on the arms and face in a 40° C. shower, however, the untreated shins were quite painful.

A third application of cream was used on the face and arms in the morning (approximately 16 hours after sun exposure). The pain has gone and the redness is very significantly reduced. On the untreated shins the skin is still red/pink and painful.

(iv) Patient 4

Here is my cream experience:

Main observation: Both my wife and I put the cream on mosquito bites and within about 10 min the itchiness went away. Applied the cream twice more the same day and the bites disappeared within one day. I have done this three times and my wife once. Other mosquito bites which were untreated stayed itchy for several days.

(v) Patient 5

I applied the cream to mosquito bites and the itchiness disappeared within 10 minutes. After a second application of the cream the bites healed with no further itchiness. At the same time I treated other mosquito bites with 1% Dermaid Cream and observed that the Dermaid Cream was not as effective as the bovine secretions cream.

(vi) Patient 6

I am a 50 year old woman and I applied the cream to my face on a daily basis. After 4 weeks my wrinkles appeared less obvious. People began to comment on my appearance after 6 weeks.

(vii) Patient 7

The bovine cell secretions cream was given to a patient with athlete's foot who self-administered it over a period of time. The patient's report on the treatment is as follows:

I used the bovine cell secretions cream to treat some athlete's foot between my little toes on my left foot. The athlete's foot was flaky skin that had been quite stubborn to heal over 12 months. I had not treated the condition in recent times. I rubbed the cream on the affected area every night for about a week. After about a week after I stopped applying the cream, I noticed that the flaky skin seemed to be less pronounced and itchy. After a further week (with no further cream being applied), the itchiness and flaky skin had gone away and has not returned for over 6 months.

(viii) Patient 8

As for my 13 year old daughter's sunburn, she got burnt with particular redness around her chest and shoulders. I thought it was bad enough that the skin would peel quite quickly. I applied the bovine cell secretions cream that evening. In the morning the redness had reduced and I applied the cream again that morning. Within 24 hours the redness had reduced visibly and the skin did not blister or peel in any obvious way. I think we applied the cream once more. No negative side effects.

Example 12. Treatment of Acne

This example demonstrates the efficacy of bovine adipose tissue-derived secretions in the treatment of acne.

Method:

A batch of bovine adipose tissue-derived secretions (hereinafter "CellFree") was produced (batch # CFB-3A) as detailed in Example 7. This CellFree was filter sterilized and then freeze dried in T175 tissue culture flasks at BTF. 100 mL of CFB-3A was placed in 2×T175 and then each flask was re-constituted with 10 mL of sterile water. The 10× concentrate was then filtered through PD10 columns, as follows:

1. Tip off the sodium azide from the top of the PD10
2. Cut the tip off the bottom of the PD10
3. Add 20 mL PBS to the top of the PD10 allow this to drain through
4. Add 2.5 mL of the concentrated CellFree to the top of the PD10
5. Allow all of the liquid to pass through the frit at the top of the PD10
6. Add 3.5 mL of PBS and place collection tube under the tip of the PD10 to collect the desalted concentrated CellFree.

27 mL was collected in total of the desalted concentrated CellFree and added to 54 grams of BP Aqueous cream (Kenkay Batch29AO1 exp May 2013).

A patch test was performed. Six human volunteers all put 200 ul of the cream on their arms and placed a band-aid over this. This was held in place for approximately 8 hours. There were no reported adverse effects from the cream.

The cream was divided into 7×10 gram in small clear plastic pots purchased from the pharmacy.

After receiving informed consent from the individuals to be involved in the trial (referred to herein as human volunteer (HV) #1 to #7), a TF-002 Acne trial form was completed for each individual and seven pots of cream were produced and one each was provided to the individuals in the trial.

According to TF-002 Acne trial protocol the individuals were given the following instructions:

This is a 21 day trial where you are required to fill in the supplied trial record form daily.

Day 1-7 do not apply the cream.

Day 8-21 You are required to apply the cream twice daily.

Please continue with your current skin treatment routine during the entire 21 days.

Score your skin once daily using the 1-6 scale below.

Record any other observations regarding your skin while using the acne cream, a list of potential considerations is included below.

Please use the table on the reverse to score your skin.

Please record your score at roughly the same time everyday.

Using the lines provided at the end of this form, please note your current skin care routine. E.g cleansing, prescribed medication or treatments from the pharmacy or supermarket.

1-6 Acne Scale

1. Clear, indicating no inflammatory lesions (red bumps, white or yellow 'squeezable' spots) or noninflammatory lesions (blackheads or whiteheads).
2. A few scattered blackheads and whiteheads and greasiness of your skin.
3. 30-40 small red bumps, blackheads and whiteheads over a quarter of your face.
4. About half of your face has small red bumps, blackheads and superficial white or yellow 'squeezable' spots.
5. Involves three quarters of your face with numerous blackheads and white or yellow 'squeezable' spots.
6. Most of your face is affected with large inflamed red lumps and or blackheads, whiteheads or white or yellow 'squeezable' spots.

Observation Considerations

1. Redness
2. Itchiness
3. Skin becomes hard
4. Skin becomes smooth
5. Skin becomes soft
6. Tingling sensation on application
7. Discolouration
8. No change Results:

| Human volunteer | Pre-treatment score (scale below) | Post treatment score (scale below) | Comments |
|---|---|---|---|
| HV#1 | 3 | 2 | Skin soft, reduction in redness, skin quite clear, no new pimples since beginning treatment |
| HV#2 | 3-4 | 2-3 | Gone from having yellow squeezable spots to a reduction in redness and no new spots |
| HV#3 | 3 | 3 | Most effective when applied to individual spots rather than whole face |
| HV#4 | 3 | 1-2 | NM found that after stopping using the cream for 5 days his skin got worse again. He has asked for more cream |
| HV#5 | 3-4 | 1 | "IH's skin is quite clear now after 4 days of use." "Cream is great. IH has had comments from teachers about it!" |
| HV#6 | 2 | 1 | Decrease redness, inflammation and pimples, reduced pimples on chest and back |
| HV#7 | 3 | 1 | Improvement in softness and smoothness |

CONCLUSION

As shown in the above table and graphically in FIG. 2, the trial acne results are positive in demonstrating an improvement in the individual trial participant's acne after administration of the composition comprising the bovine adipose tissue-derived secretions.

The invention claimed is:

1. A method of treating acne in a subject in need thereof, comprising topically administering to the subject a pharmaceutical composition comprising an effective amount of adipose tissue-derived secretions, in combination with a pharmaceutically-acceptable carrier or diluent,
wherein the adipose tissue-derived secretions are prepared by:
(i) exposing a sample of bovine adipose tissue to a proteolytic enzyme solution to generate a cell suspension;
(ii) centrifuging the suspension of cells to form a cell pellet, a free lipid layer above a floating cell layer which comprises adipocytes and an intermediate layer between the cell pellet and the floating cell layer, said intermediate layer being depleted of cells relative to the cell pellet and the floating cell layer; and
(iii) removing the free lipid layer and the intermediate layer;
(iv) optionally removing adipocytes from the centrifuged material by removing part or all of the floating cell layer which comprises adipocytes;
(v) mixing the cell pellet and, if present, the floating cell layer comprising adipocytes, to form an adipose tissue derived cell suspension which may or may not include adipocytes;
(vi) culturing the cell suspension under appropriate conditions;
(vii) collecting a supernatant of the cell culture to obtain the adipose tissue-derived secretions.

2. The method according to claim 1, wherein the subject has clinically relevant acne.

3. The method according to claim 1, wherein the proteolytic enzyme solution comprises collagenase at a final concentration of about 0.25% w/v.

4. The method according to claim 1, wherein culturing the cell suspension comprises culturing (i) an adherent cell culture, or (ii) a spinner culture.

5. The method according to claim 4, wherein said adherent cell culture is a confluent cell culture.

6. The method according to claim 1, further comprising freeze-drying said bovine adipose tissue-derived secretions after said harvesting.

7. The method according to claim 6, further comprising re-hydrating said freeze-dried material.

* * * * *